US010335225B2

(12) United States Patent
Hacker et al.

(10) Patent No.: US 10,335,225 B2
(45) Date of Patent: Jul. 2, 2019

(54) ELECTROSURGICAL MEDICAL DEVICE HANDPIECE WITH INSULATED ASPIRATION SYSTEM

(71) Applicant: Arthrex, Inc., Naples, FL (US)

(72) Inventors: Randall L. Hacker, Naples, FL (US); Jeremiah D. Caldwell, Naples, FL (US); Leander Rivera, Naples, FL (US); Richard J. Taft, Naples, FL (US)

(73) Assignee: Arthrex, Inc., Naples, FL (US)

( * ) Notice: Subject to any disclaimer, the term of this patent is extended or adjusted under 35 U.S.C. 154(b) by 268 days.

(21) Appl. No.: 15/357,560

(22) Filed: Nov. 21, 2016

(65) Prior Publication Data

US 2018/0140349 A1    May 24, 2018

(51) Int. Cl.
*A61B 18/14*    (2006.01)
*A61B 18/00*    (2006.01)

(52) U.S. Cl.
CPC ............ *A61B 18/14* (2013.01); *A61B 18/148* (2013.01); *A61B 2018/00101* (2013.01);
(Continued)

(58) Field of Classification Search
CPC .......... A61B 18/14; A61B 2018/00101; A61B 2018/00577; A61B 2018/1467; A61B 2218/007
See application file for complete search history.

(56) References Cited

U.S. PATENT DOCUMENTS 3,630,203 A * 12/1971 Sellinger ............ A61B 18/0218
606/24
4,936,281 A    6/1990 Stasz
(Continued)

FOREIGN PATENT DOCUMENTS

AU    2007226692    9/2007
AU    2011215911    8/2011
(Continued)

OTHER PUBLICATIONS

Patent Cooperation Treaty, "International Search Report and Written Opinion", issued in International Application No. PCT/US2017/048114, by U.S. Searching Authority, document of 15 pages, dated Oct. 30, 2017.

(Continued)

*Primary Examiner* — Daniel W Fowler
(74) *Attorney, Agent, or Firm* — Akerman LLP; Michael K. Dixon

(57) ABSTRACT

An electrosurgical instrument for the treatment of tissue via an electrode assembly is disclosed having at least one active electrode and an aspiration system for configured to collect aspirated materials and to remove those aspirated materials from a surgical site while preventing the materials from melting and thereby clogging the aspiration system. In at least one embodiment, the aspiration system may include an internal aspiration collection chamber positioned at a distal end of the instrument to collect aspirated material and insulate the aspirated material to prevent the aspirated material from melting within the aspiration system and thereby clogging the aspiration system. The internal aspiration collection chamber may also be subjected to reduced heating from the active electrode by limiting the exposure of the internal aspiration collection chamber to a minimally sized support arm extending from active electrode to the channel of the aspiration system in the electrosurgical instrument shaft.

20 Claims, 6 Drawing Sheets

(52) U.S. Cl.
CPC ............... *A61B 2018/00577* (2013.01); *A61B 2018/1467* (2013.01); *A61B 2218/007* (2013.01)

(56) References Cited

U.S. PATENT DOCUMENTS

| | | | |
|---|---|---|---|
| 5,486,161 A | 1/1996 | Lax et al. | |
| 5,843,019 A * | 12/1998 | Eggers | A61B 18/12 604/22 |
| 5,902,272 A | 5/1999 | Eggers et al. | |
| 6,027,501 A | 2/2000 | Goble et al. | |
| 6,234,178 B1 | 5/2001 | Goble et al. | |
| 6,251,121 B1 | 6/2001 | Saadat | |
| 6,277,114 B1 | 8/2001 | Bullivant et al. | |
| 6,296,638 B1 | 10/2001 | Davison et al. | |
| 6,394,956 B1 | 5/2002 | Chandrasekaran et al. | |
| 6,517,534 B1 | 2/2003 | Mcgovern et al. | |
| 6,638,222 B2 | 10/2003 | Chandrasekaran et al. | |
| 6,726,684 B1 | 4/2004 | Woloszko et al. | |
| 6,743,226 B2 | 6/2004 | Cosman et al. | |
| 6,878,149 B2 | 4/2005 | Gatto | |
| 7,481,807 B2 * | 1/2009 | Knudsen | A61B 18/148 606/41 |
| 8,066,704 B2 | 11/2011 | DeCesare et al. | |
| 8,292,887 B2 | 10/2012 | Woloszko et al. | |
| 8,747,400 B2 * | 6/2014 | Bigley | A61B 18/042 606/41 |
| 9,011,426 B2 | 4/2015 | Van Wyk | |
| 9,125,666 B2 | 9/2015 | Steinke et al. | |
| 9,168,082 B2 | 10/2015 | Evans et al. | |
| 9,254,166 B2 * | 2/2016 | Aluru | A61B 18/14 |
| 9,271,784 B2 | 3/2016 | Evans et al. | |
| 2005/0065510 A1 | 3/2005 | Carmel et al. | |
| 2006/0259025 A1 | 11/2006 | Dahla | |
| 2007/0106288 A1 | 5/2007 | Woloszko et al. | |
| 2007/0213704 A1 | 9/2007 | Truckai et al. | |
| 2009/0048592 A1 * | 2/2009 | Thomas | A61B 18/148 606/33 |
| 2010/0023008 A1 * | 1/2010 | Heard | A61B 18/1485 606/49 |
| 2010/0082026 A1 * | 4/2010 | Curtis | 606/33 |
| 2013/0185922 A1 * | 7/2013 | Twomey | A61B 18/1445 29/527.1 |
| 2013/0310823 A1 | 11/2013 | Gelfand et al. | |

FOREIGN PATENT DOCUMENTS

| | | |
|---|---|---|
| GB | 2327352 | 1/1999 |
| WO | 02085230 | 10/2002 |
| WO | 2005039390 | 5/2005 |

OTHER PUBLICATIONS

Arthrex, Inc., "CoolCut™ Radio Frequency Ablation," arthrex.com, accessed: Jun. 2016, document of 4 pages. http://www.arthrex.com/imaging-resection/coolcut-radio-frequency-ablation.

Misonix, Inc., "Sonastar™," misonix.com, Nov. 4, 2015, document of 3 pages. http://web.archive.org/web/20151104094209/http://misonix.com/portfolio-items/sonastar/.

* cited by examiner

ELECTROSURGICAL MEDICAL DEVICE HANDPIECE WITH INSULATED ASPIRATION SYSTEM

FIELD OF THE INVENTION

The disclosure relates generally to electrosurgical medical devices, and more particularly, to electrosurgical medical devices configured to ablate tissue on patients in surgical procedures.

BACKGROUND

Ablation devices have been used to remove tissue within patients in a variety of medical procedures. Many ablation devices include aspiration systems for removing ablated tissue and fluids from surgical sites. Some devices include aspiration systems within the ablation handpiece and include aspiration inlets at a distal tip of the ablation handpiece. The ablation materials are aspirated through the aspiration inlets at a distal tip and into the aspiration system, where the material is collected and later removed. Many of these conventional aspiration systems clog up and become unusable during surgical procedures. Often times, aspects of the aspiration system at a distal tip of an ablation handpiece becomes clogged because those aspects of the aspiration system are heated by the active electrode to such an extent that the aspirated materials in the aspiration system melt to the walls of the aspiration system. The melted aspiration material proves to be very problematic for the ablation devices. Thus, a need exists for a more robust aspiration system for a handheld ablation device.

SUMMARY OF THE INVENTION

An electrosurgical instrument for the treatment of tissue via an electrode assembly is disclosed having at least one active electrode and an aspiration system for configured to collect aspirated materials and to remove those aspirated materials from a surgical site while preventing the materials from melting and thereby clogging the aspiration system. In at least one embodiment, the aspiration system may include an internal aspiration collection chamber positioned at a distal end of the instrument to collect aspirated material and insulate the aspirated material to prevent the aspirated material from melting within the aspiration system and thereby clogging the aspiration system. The internal aspiration collection chamber may also be subjected to reduced heating from the active electrode by limiting the exposure of the internal aspiration collection chamber to a minimally sized support arm extending from active electrode to the channel of the aspiration system positioned within the shaft of the electrosurgical instrument. The aspiration system may be formed from one or more insulating materials to reduce, if not eliminate, melting of aspirated materials. The aspiration system may be maintained in position within the shaft of the electrosurgical instrument via an expanded material having been injected into a cavity between the aspiration system and the shaft. The electrosurgical instrument may also be configured to operate more efficiently than conventional systems via the active electrode having a sandblasted roughened surface to provide consistent performance beginning at startup without need for a warm up period.

In at least one embodiment, the electrosurgical instrument for the treatment of tissue may include a shaft, an electrode assembly, one or more active electrodes and one or more return electrode separated from the active electrode via at least one insulator. The electrosurgical instrument may include one or more insulators forming an internal aspiration collection chamber configured to received aspirated material from a surgical site and to pass the aspirated material on within the electrosurgical instrument. The internal aspiration collection chamber may be in fluid communication with one or more aspiration inlets. The electrosurgical instrument may include an aspiration system for removing material from a surgical site, the aspiration system including one or more conduits formed by a channel extending through the shaft, the internal aspiration collection chamber and the aspiration inlet.

The insulator may be formed from a nonconductive material, such as, but not limited to, ceramic, to maintain a temperature below a lowest melting point of any material within the aspirated materials. The insulator may be coupled to a distal tip of the channel of the aspiration system and support the active electrode having a substantially planar outer surface that is nonorthogonal to a longitudinal axis of the channel of the aspiration system. The substantially planar outer surface of the at least one active electrode may be positioned generally parallel to the longitudinal axis of the channel of the aspiration system. The outer surface of the active electrode may be separated from the shaft of the electrosurgical instrument by the insulator.

The active electrode may include a support arm extending from a substantially planar outer surface of the active electrode inwardly toward a longitudinal axis of the channel of the aspiration system whereby the support arm includes a threaded support orifice configured to be threadably attached to threads at a distal end of the channel of the aspiration system. The threaded support orifice may couple the internal aspiration collection chamber of the aspiration system to the conduit of the aspiration system.

A longitudinal axis of the internal aspiration collection chamber within the insulator may be positioned nonparallel with a longitudinal axis of the channel of the aspiration system. A longitudinal axis of the internal aspiration collection chamber within the at least one insulator may be positioned orthogonal with a longitudinal axis of the channel of the aspiration system. The internal aspiration collection chamber may be an elongated chamber defined at least in part by a distal, linear surface, a first proximal, linear surface and a second proximal, linear surface. The distal, linear surface may be aligned with the first and second proximal, linear surfaces and are each aligned with a longitudinal axis of the internal aspiration collection chamber, wherein the longitudinal axis of the internal aspiration collection chamber may be positioned orthogonal to a longitudinal axis of the channel of the aspiration system. The internal aspiration collection chamber may be formed from a first section and a second section, whereby the first section has a larger cross-sectional area than the second section and the first section is positioned closer to the active electrode than the second section. The insulator may include a pocket into which a portion of the support arm of the active electrode extends, wherein a proximally facing surface of the active electrode contacts a distally facing surface of the insulator and forces a proximally facing surface of the insulator to contact a distally facing surface of the electrosurgical instrument, thereby securing the active electrode and the insulator to the shaft of the electrosurgical instrument by enabling the support arm of the active electrode to secure the insulator to the shaft of the electrosurgical instrument when the support arm of the active electrode is threaded onto the shaft of the electrosurgical instrument.

The electrosurgical instrument may also be configured to operate more efficiently than conventional systems via the active electrode having a roughened surface, such as, but not limited to, a sandblasted outer surface, to provide consistent performance beginning at startup without need for a warm up period. With a roughened surface, the active electrode operates consistently throughout the startup period and through steady state operations.

The electrosurgical instrument may be configured such that a position of the channel forming a portion of the conduit of the aspiration system is maintained via an expanded material having been injected into a cavity between the channel and the shaft. In at least one embodiment, the aspiration system may be maintained in position within the shaft via injection overmolding.

An advantage of the electrosurgical instrument is that the electrosurgical instrument includes a nonconductive internal aspiration collection chamber configured to collect aspirated materials and to remove those aspirated materials from a surgical site while preventing the aspirated materials from melting and thereby clogging the aspiration system. Another advantage of the electrosurgical instrument is that the insulator forming the internal aspiration collection chamber has minimal contact with the active electrode, thereby reducing heating of the insulator and the internal aspiration collection chamber.

Yet another advantage of the electro surgical instrument is that the active electrode includes a roughened surface, such as, but not limited to, a sandblasted outer surface, to provide consistent performance beginning at startup without need for a warm up period, thereby operating more efficiently than conventional systems.

Another advantage of the electrosurgical instrument is that the electrosurgical instrument may be configured such that a position of the channel forming a portion of the aspiration system may be maintained via an expanded material having been injected into a cavity between the channel and the shaft, thereby nearly, if not completely, eliminating any movement of components within the outer shaft of the electrosurgical instrument.

These and other embodiments are described in more detail below.

DETAILED DESCRIPTION OF THE FIGURES

Figure 1:
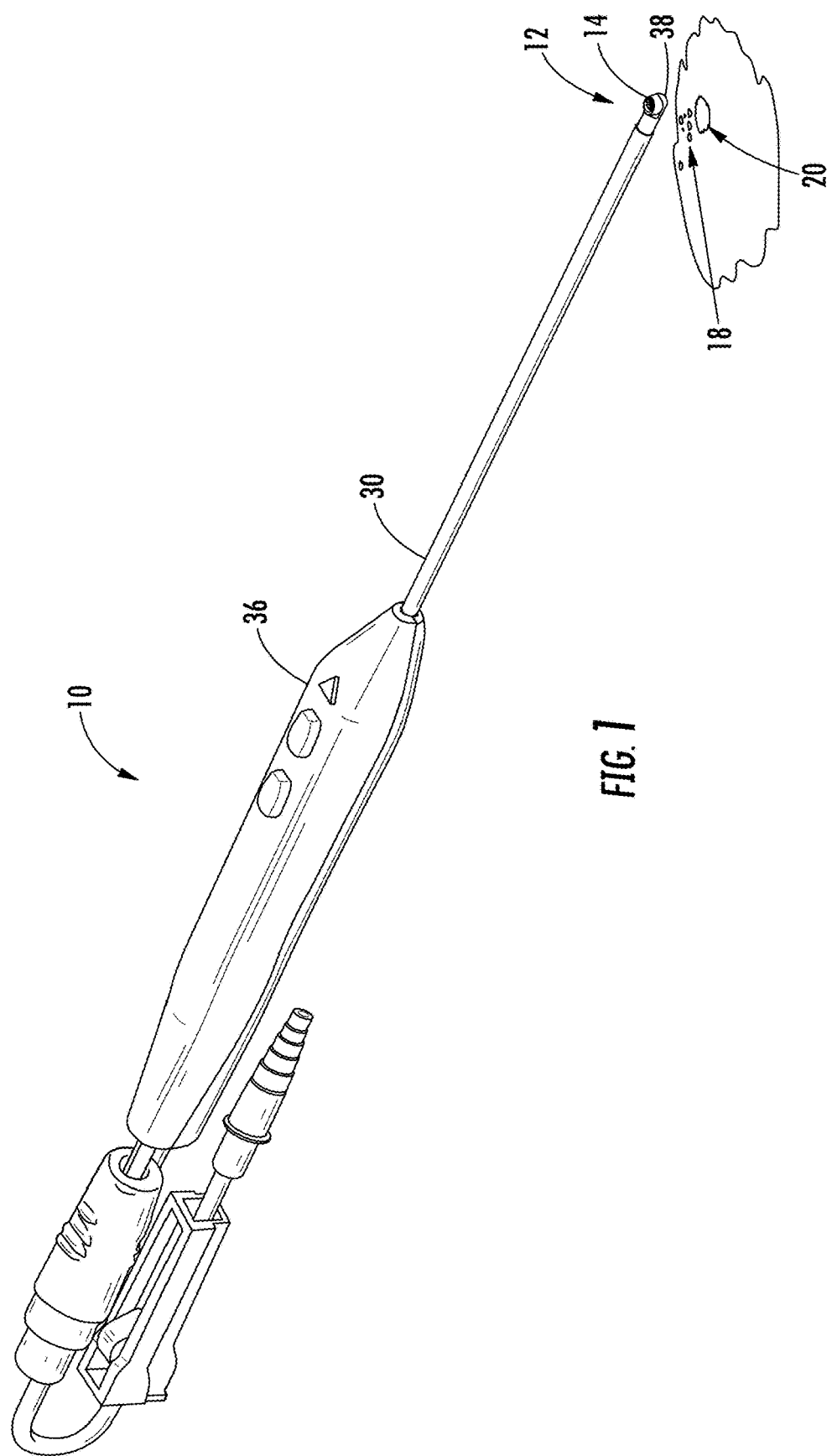
FIG. 1 is a perspective view of the electrosurgical instrument for the treatment of tissue via an electrode assembly.

As shown in FIGS. 1-6, an electrosurgical instrument 10 for the treatment of tissue via an electrode assembly 12 is disclosed having at least one active electrode 14 and an aspiration system 16 for configured to collect aspirated materials and to remove those aspirated materials 18 from a surgical site 20 while preventing the materials 18 from melting and thereby clogging the aspiration system 16. In at least one embodiment, the aspiration system 16 may include an internal aspiration collection chamber 22 positioned at a distal end 24 of the instrument 10 to collect aspirated material 18 and insulate the aspirated material 18 to prevent the aspirated material 18 from melting within the aspiration system 16 and thereby clogging the aspiration system 16. The internal aspiration collection chamber 22 may also be subjected to reduced heating from the active electrode 14 by limiting the exposure of the internal aspiration collection chamber 22 to a minimally sized support arm 26 extending from active electrode 14 to the channel 28 of the aspiration system 16 positioned within the shaft 30 of the electrosurgical instrument 10. The aspiration system 16 may be formed from one or more insulating materials to reduce, if not eliminate, melting of aspirated materials. The aspiration system 16 may be maintained in position within the shaft 30 of the electrosurgical instrument 10 via an expanded material having been injected into a cavity 32 between the aspiration system 16 and the shaft 30. The electrosurgical instrument 10 may also be configured to operate more efficiently than conventional systems via the active electrode 14 having a sandblasted roughened surface 42 to provide consistent performance beginning at startup without need for a warm up period.

Figure 2:
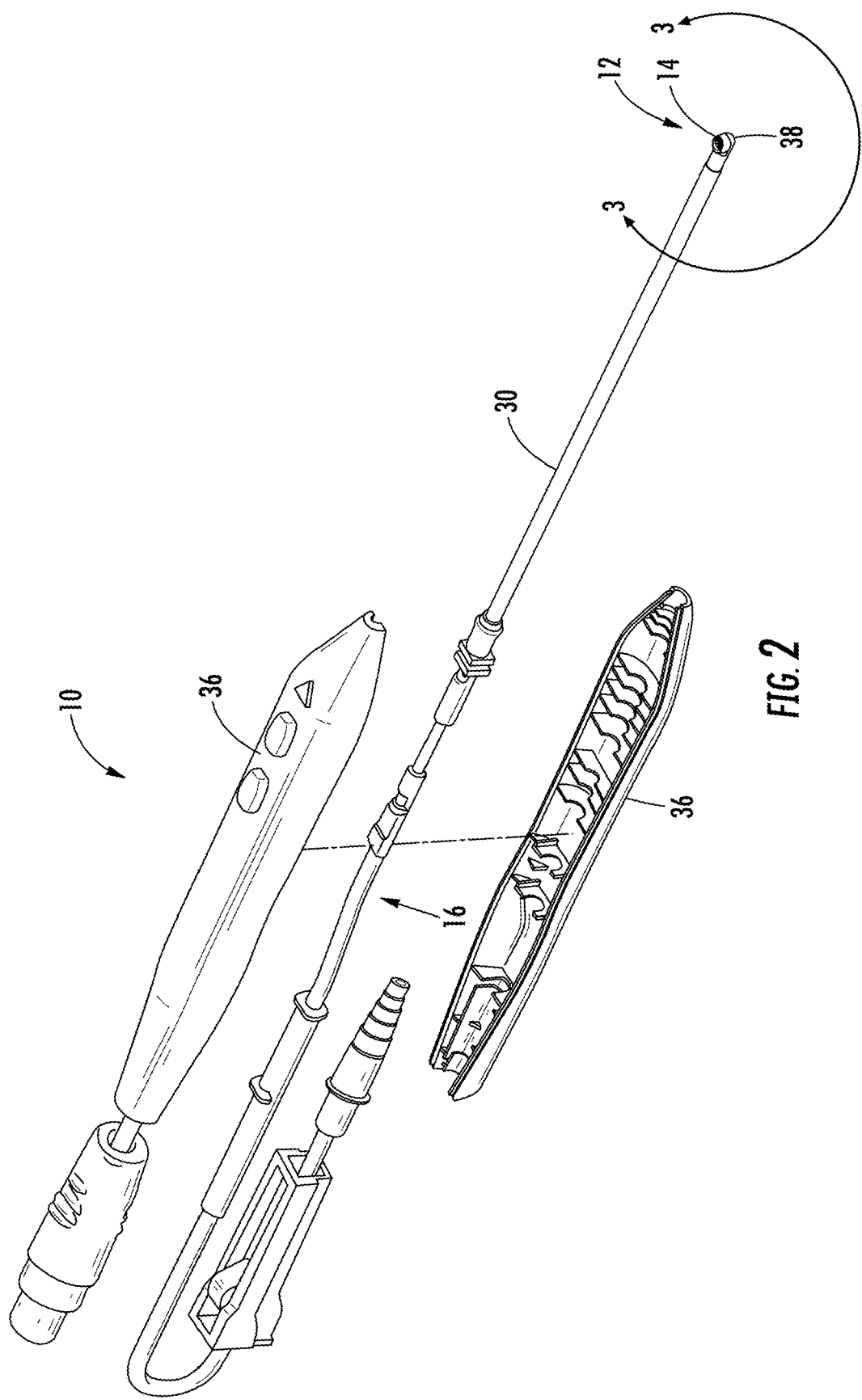
FIG. 2 is an exploded perspective view of the electrosurgical instrument shown in FIG. 1.
Figure 3:
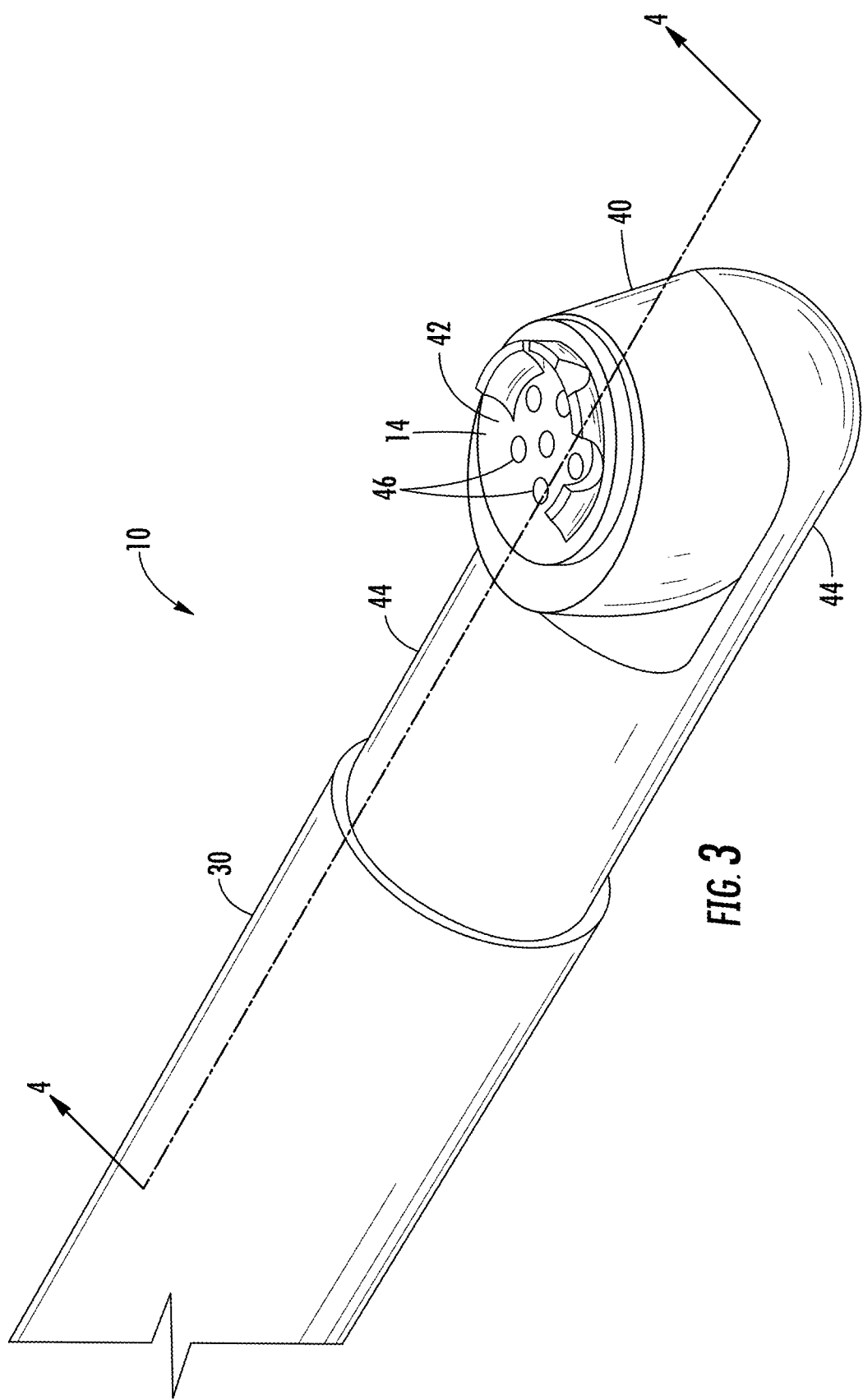
FIG. 3 is a detail view of a distal end of the electrosurgical instrument taken at detail line 3-3 in FIG. 2.

In at least one embodiment, the electrosurgical instrument 10 may include a shaft 30 extending distally from a handle 36, as shown in FIGS. 1 and 2. The shaft 30 may have any appropriate size and configuration to support the electrode assembly 12 and to facilitate use of the electrode assembly 12 during surgical procedures. The handle 36 likewise may have any appropriate size and configuration to support the electrode assembly 12 and to facilitate use of the electrode assembly 12 during surgical procedures. The shaft 30 and handle 36 may be formed from any appropriate material.

The electrosurgical instrument 10 may include an electrode assembly 12 formed by one or more active electrodes 14 and one or more return electrodes 38, as shown in FIGS. 1-6. The return electrode 38 may be separated from the active electrode 14 via at least one insulator 40. The active electrode 14 may be positioned on a distal end 42 of the internal aspiration collection chamber 22 with at least one outer surface 42 exposed. The return electrode 38 may be positioned near the distal end 42 of the internal aspiration collection chamber 22 but separated from the active electrode 14 via the insulator 40. The return electrode 38 may be include at least one outer surface 44 exposed. In at least one embodiment, the insulator 40 may form an internal aspiration collection chamber 22 configured to received aspirated material 18 from a surgical site 20 and to pass the aspirated material 18 on within the electro surgical instrument 10. The internal aspiration collection chamber 22 may be in fluid communication with at least one aspiration inlet 46. The electrosurgical instrument 10 may include an aspiration system 16 for removing material 18 from a surgical site 20 whereby the aspiration system 16 includes one or more conduits 48 formed by a channel 28 extending through the shaft 30, the internal aspiration collection chamber 22 and the aspiration inlet 46.

In at least one embodiment, the outer surface 42 of the active electrode 14 may be configured to promote energy transfer between the active electrode 14 and the return electrode 38. The insulator 40 may be coupled to a distal tip 50 of the channel 28 of the aspiration system 16 and may support the active electrode 14. The active electrode 14 may include an outer surface 42, which may be substantially planar, that is nonorthogonal to a longitudinal axis 52 of the channel 28 of the aspiration system 16. The substantially planar outer surface 42 of the active electrode 14 may be positioned generally parallel to the longitudinal axis 52 of the channel 28 of the aspiration system 16. The outer surface 42 may be separated from the shaft 30 of the electrosurgical instrument 10 by the insulator 40.

Figure 4:
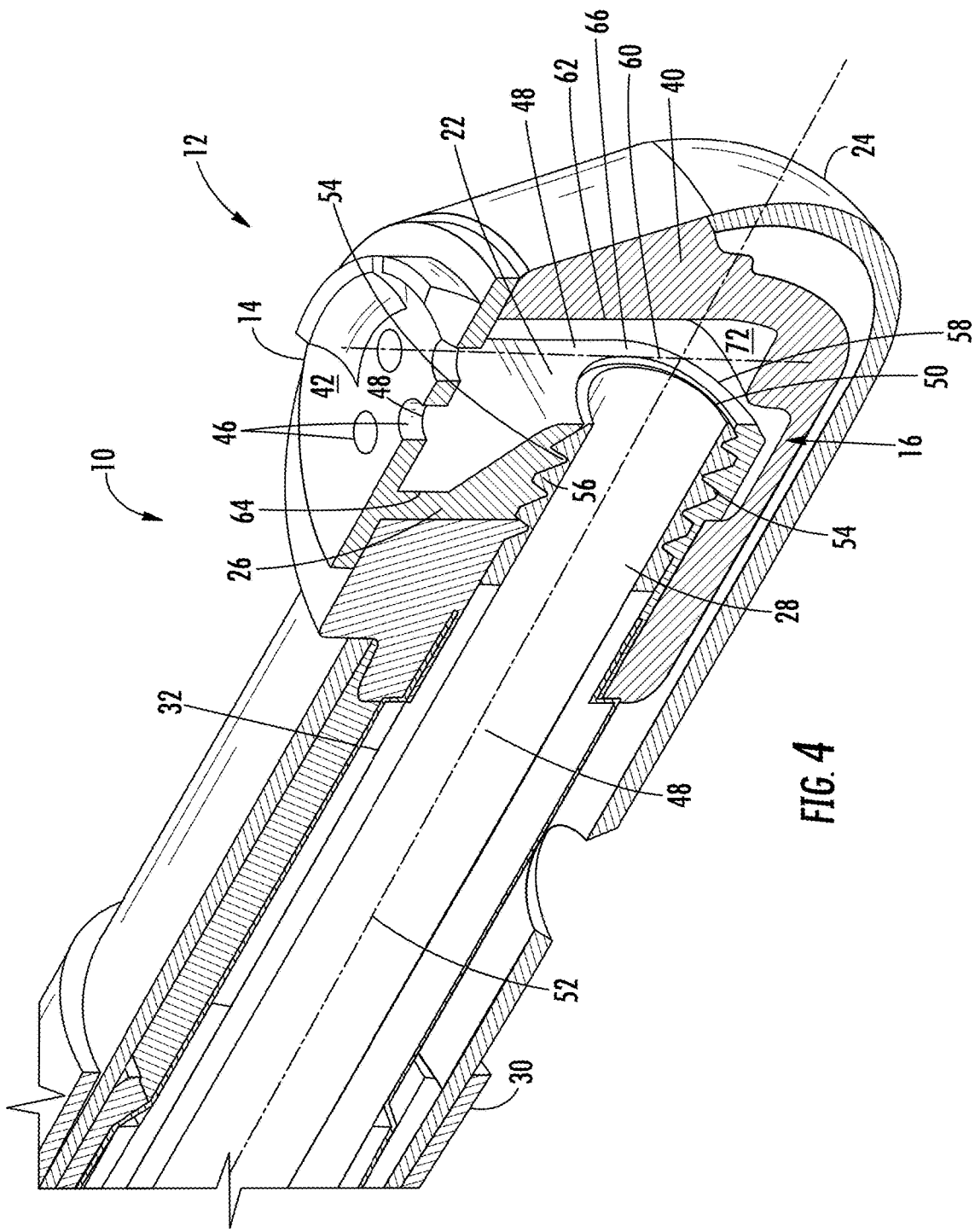
FIG. 4 is a cross-sectional, perspective view of the distal end of the electrosurgical instrument taken at section line 4-4 in FIG. 3.
Figure 5:
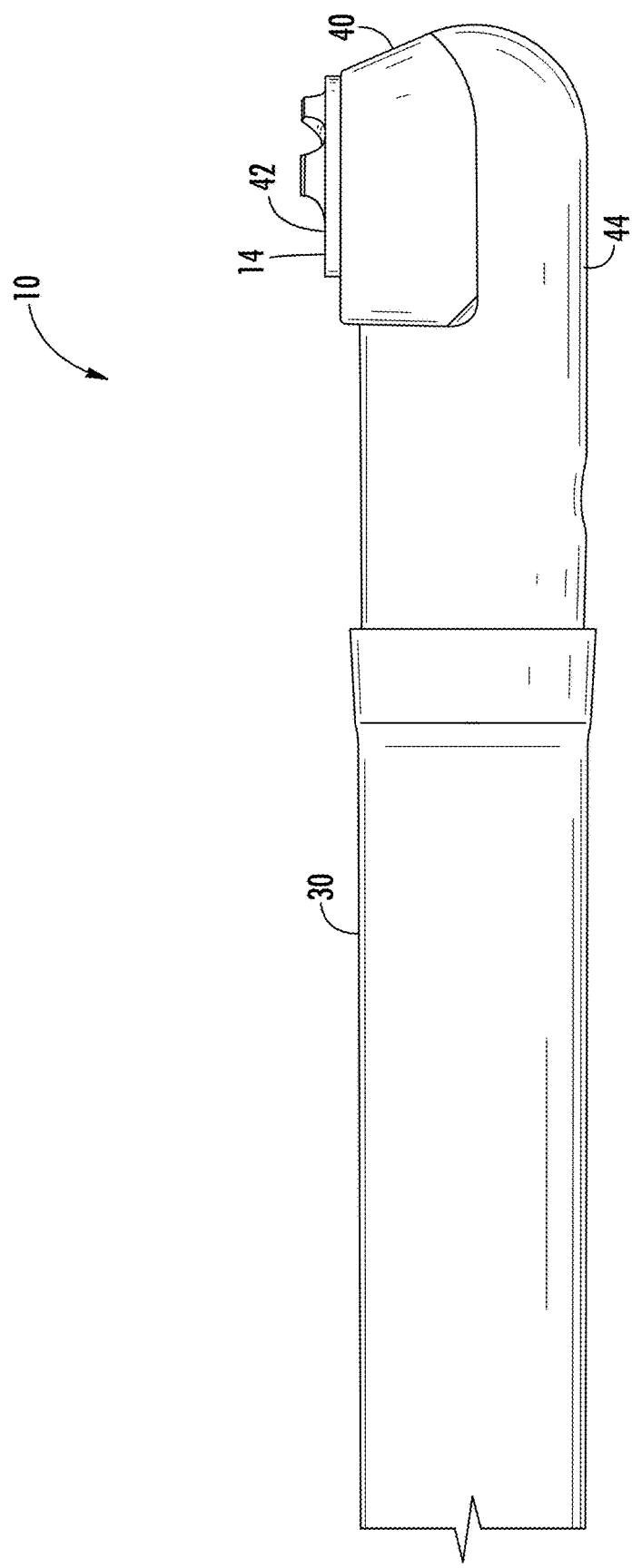
FIG. 5 is a side view of the distal end of the electrosurgical instrument.
Figure 6:
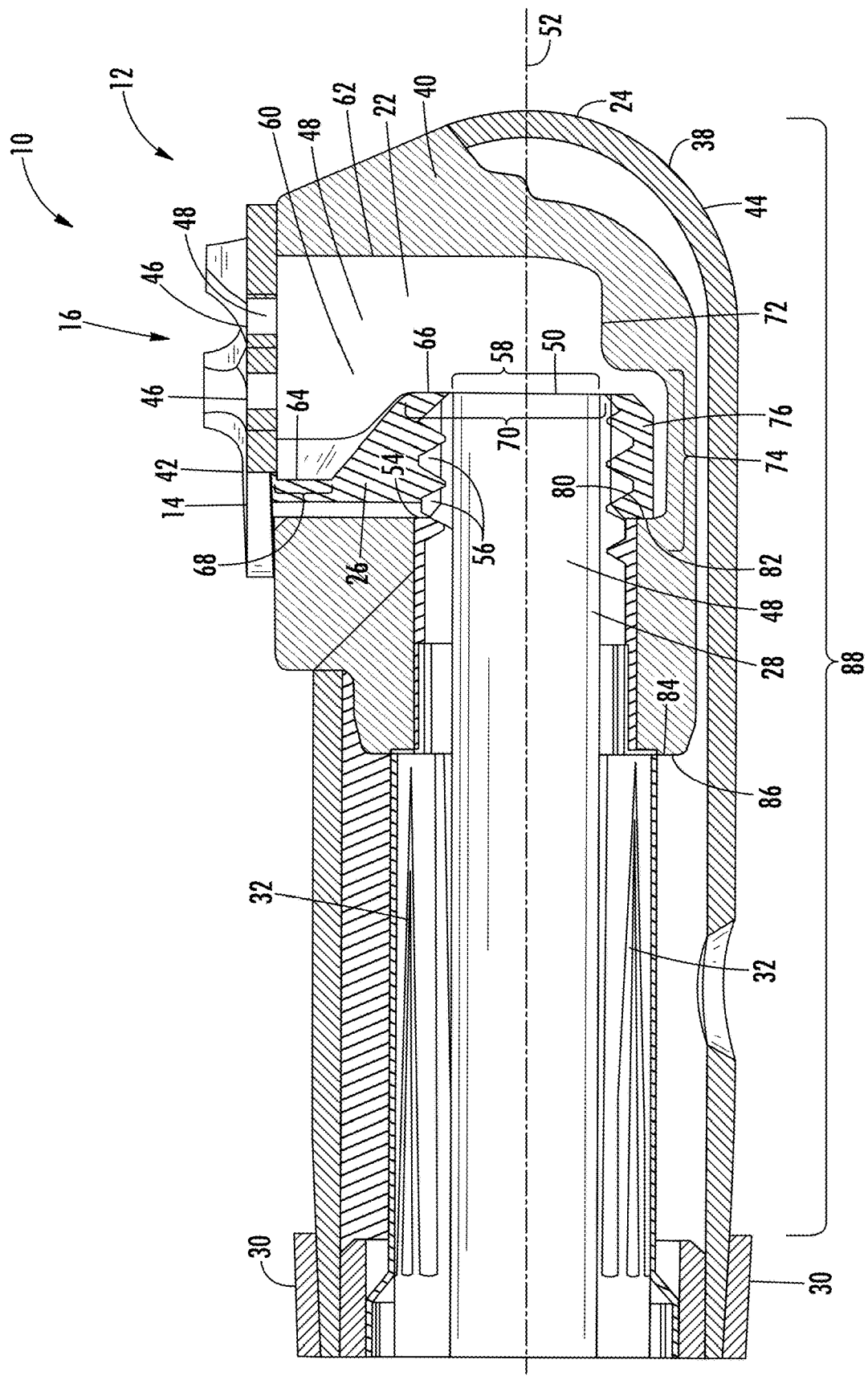
FIG. 6 is a cross-sectional, side view of the distal end of the electrosurgical instrument taken at section line 4-4 in FIG. 3.

In at least one embodiment, the active electrode 14 may include a support arm 26, as shown in FIGS. 4 and 6, extending from the substantially planar outer surface 42 of the active electrode 14 inwardly toward the longitudinal axis 52 of the channel 28 of the aspiration system 16. The support arm 26 may include a threaded support orifice 54 configured to be threadably attached to threads 56 at a distal end 50 of the channel 28 of the aspiration system 20. The threaded support orifice 54 may couple the internal aspiration collection chamber 22 of the aspiration system 16 to the channel 28 of the aspiration system 16. In at least one embodiment, the support arm 26 may be aligned with one or more outlets 58 of the internal aspiration collection chamber 22. In at least one embodiment, the internal aspiration collection chamber 22 may include a single outlet 58 coupled to the channel 28. The outlet 58 may be, but is not limited to, having a tubular configuration. The single tubular outlet 58 may extend orthogonal from a sidewall forming the internal aspiration collection chamber 22. The single tubular outlet 58 may be configured to have minimal contact with the active electrode 14 to limit the amount of ablation heat transferred from the active electrode 14 to the proximal shaft 30 forming a portion of the internal aspiration system 16 to reduce the likelihood of tissue melting within the internal aspiration system 16.

In at least one embodiment, the internal aspiration collection chamber 22 may be formed by the insulator 40, as shown in FIGS. 4 and 6. The insulator 40 may be formed from one or more nonconductive materials, such as, but not limited to, ceramic. In at least one embodiment, the internal aspiration collection chamber 22 may function as the insulator 40. The internal aspiration collection chamber 22 may separate the active return electrodes 14, 38 and may be configured to direct aspirated materials 18, such as, but not limited to, aspirated fluids and tissue, from the surgical site 20 and into the aspiration channel 28 within the shaft 30 of the electrosurgical instrument 10. In embodiments in which internal aspiration collection chamber 22 is formed from ceramic, the ceramic internal aspiration collection chamber 22 does not absorb as much heat from the ablation process than if the component were formed from metal. As a result, the electrosurgical instrument 10 works far better than conventional systems formed from metal. The internal aspiration collection chamber 22 prevents tissue aspirated within the aspiration system 16 from being melted onto the walls of the aspiration system 16. In conventional systems, tissue aspirated within an aspiration system melts onto the walls of the aspiration system, thereby clogging the system. In contrast, the internal aspiration collection chamber 22 prevents clogging of the aspiration system 16 by preventing tissue aspirated within the aspiration system 16 from being melted onto the walls of the aspiration system 16.

The internal aspiration collection chamber 22 may be configured such that a longitudinal axis 60 of the internal aspiration collection chamber 22 may be positioned nonparallel with the longitudinal axis 52 of the channel 28 of the aspiration system 16. In at least one embodiment, the longitudinal axis 60 of the internal aspiration collection chamber 22 may be positioned orthogonal to a longitudinal axis 52 of the channel 28 of the aspiration system 16. The internal aspiration collection chamber 22 may be an elongated chamber defined at least in part by a distal, linear surface 62, a first proximal, linear surface 64 and a second proximal, linear surface 66. The distal, linear surface 62 may be aligned with the first and second proximal, linear surfaces 64, 66 and are each aligned with a longitudinal axis 60 of the internal aspiration collection chamber 22, whereby the longitudinal axis 60 of the internal aspiration collection chamber 22 may be positioned orthogonal to the longitudinal axis 52 of the channel 28 of the aspiration system 16. As shown in FIG. 6, the internal aspiration collection chamber 22 may be formed from a first section 68 and a second section 70, whereby the first section 68 has a larger cross-sectional area than the second section 70, and the first section 68 is positioned closer to the at least one active electrode 14 than the second section 70. The cross-sectional areas extend in a plane orthogonal to the longitudinal axis 60 of the internal aspiration collection chamber 22. The first section 68 may be positioned between the active electrode 14 and the second section 70 such that material flowing in the aspiration system 16 through the active electrode 14 first enters the first section 68 before entering the second section 70. The first and second sections 68, 70 may be formed, in part, by the distal, linear surface 62 extending from the active electrode 14 to a bottom surface 72 of the internal aspiration collection chamber 22. The shortest distance between the distal, linear surface 62 and a second proximal, linear surface 66 forming a portion of the second section 70 is less than the shortest distance between the distal, linear surface 62 and a first proximal, linear surface 64 forming a portion of the first section 68. As such, the second proximal, linear surface 66 may be positioned closer to the longitudinal axis 60 of the internal aspiration collection chamber 22 than the first proximal, linear surface 64.

The insulator 40 may be configured such that when the insulator 40 and support arm 26 are threaded onto the distal end 50 of the channel 28, the insulator 40 is firmly attached to the shaft 30 through a portion of the insulator 40 being held via interference. In particular, as shown in FIG. 6, the insulator 40 may include a pocket 74 into which a portion 76 of the support arm 26 of the active electrode 14 extends. A proximally facing surface 80 of the active electrode 14 may contact a distally facing surface 82 of the insulator 40 and forces a proximally facing surface 84 of the insulator 40 to contact a distally facing surface 86 of the electrosurgical instrument 10, thereby securing the active electrode 14 and the insulator 40 to the shaft 30 of the electrosurgical instrument 10 by enabling the support arm 26 of the active electrode 14 to secure the insulator 40 to the shaft 30 of the electrosurgical instrument 10 when the support arm 26 of the active electrode 14 is threaded onto the shaft 30 of the electrosurgical instrument 10.

The electrosurgical instrument 10 may be configured such that a position of the channel 28 forming a portion of the conduit 48 of the aspiration system 16 is maintained via an expanded material having been injected into a cavity 32 between the channel 28 and the shaft 30. In particular, the aspiration system 16 may be maintained in position within the shaft 30 via injection overmolding. For instance, after the electrosurgical instrument 10 has been assembled with the channel 28 of the fluid aspiration system 16 installed within the outer tubular shaft 30 and the distal tip 88, formed from the insulator 40 with the active electrode 14 and return electrode 38, attached to the fluid aspiration channel 28 and the outer tubular housing, the one or more interior cavities 32 may be injected with a liquid material that expands completely within the interior cavities 32 providing electrical insulation and structural support to the components within the outer shaft 30 of the electrosurgical instrument 10.

In at least one embodiment, the outer surface 42 of the active electrode 14 may be a roughened surface, such as, but not limited to, a sandblasted roughened surface. The roughened outer surface 42 of the active electrode 14 may increase the surface area and provide a more consistent performance of the electrosurgical instrument 10 at startup. Conventional designs without a sandblasted outer surface of the active electrode only operate consistently after about one minute of use. When the outer surface of the active electrode 14 is sandblasted, the electrosurgical instrument 10 provided consistent performance beginning at startup and did not need a warm up period.

During use, the electrosurgical instrument 10 may be used to ablate tissue from a surgical site 20. The active electrode 14 may be powered by and controlled by any appropriate electrosurgical control unit. The roughened outer surface 42 of the active electrode 14 operates consistently through startup conditions and at steady state operation. While the active electrode 14 is ablating tissue, the aspiration system 16 may be activated to remove tissue, fluids and other material from the surgical site 20. The aspiration system 16 may be attached to a suction generator (not shown). The aspiration system 16 may draw materials through one or more aspiration inlets 46, which may be, but is not required to be, positioned within the active electrode 14. The materials flow through the aspiration inlet 46 and collect within the internal aspiration collection chamber 22. Because the internal aspiration collection chamber 22 is formed from one or more nonconductive materials, such as, but not limited to, ceramic, the inner surfaces, specifically, the distal, linear surface 62, the first proximal linear surface 64, the second linear surface 66 and the bottom surface 72, remain at a temperature lower than a melting point of the aspirated materials. As such, the aspirated materials do not melt in the internal aspiration collection chamber 22 and thus do not clog up the aspiration system 16. Such configuration greatly enhances the operational efficiency of the electrosurgical instrument 10.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. An electrosurgical instrument for the treatment of tissue, comprising:
   a shaft;
   an electrode assembly, comprising:
      at least one active electrode;
      at least one return electrode separated from the active electrode via at least one insulator;
      the at least one insulator forming an internal aspiration collection chamber configured to received aspirated material from a surgical site and to pass the aspirated material on within the electrosurgical instrument;
      wherein the internal aspiration collection chamber is in fluid communication with at least one aspiration inlet; and
   an aspiration system for removing material from a surgical site, the aspiration system including at least one conduit formed by a channel extending through the shaft, the internal aspiration collection chamber and the at least one aspiration inlet;
   wherein the at least one active electrode includes a support arm extending from a substantially planar outer surface of the at least one active electrode inwardly toward a longitudinal axis of the channel of the aspiration system whereby the support arm includes a threaded support orifice configured to be threadably attached to threads at a distal end of the channel of the aspiration system.

2. The electrosurgical instrument of claim 1, wherein an outer surface of the at least one active electrode is separated from the shaft of the electrosurgical instrument by the at least one insulator.

3. The electrosurgical instrument of claim 1, wherein the threaded support orifice couples the internal aspiration collection chamber of the aspiration system to the at least one channel of the aspiration system.

4. The electrosurgical instrument of claim 1, wherein a longitudinal axis of the internal aspiration collection chamber is positioned nonparallel with a longitudinal axis of the channel of the aspiration system.

5. The electrosurgical instrument of claim 1, wherein a longitudinal axis of the internal aspiration collection chamber is positioned orthogonal with a longitudinal axis of the channel of the aspiration system.

6. The electrosurgical instrument of claim 1, wherein the internal aspiration collection chamber is an elongated chamber defined at least in part by a distal, linear surface, a first proximal, linear surface and a second proximal, linear surface.

7. The electrosurgical instrument of claim 6, wherein the distal, linear surface is aligned with the first and second proximal, linear surfaces and are each aligned with a longitudinal axis of the internal aspiration collection chamber, wherein the longitudinal axis of the internal aspiration collection chamber is positioned orthogonal to a longitudinal axis of the channel of the aspiration system.

8. The electrosurgical instrument of claim 6, wherein the internal aspiration collection chamber is formed from a first section and a second section, whereby the first section has a larger cross-sectional area than the second section and the first section is positioned closer to the at least one active electrode than the second section.

9. The electrosurgical instrument of claim 1, wherein an outer surface of the active electrode is a sandblasted roughened surface.

10. The electrosurgical instrument of claim 1, wherein the at least one insulator is formed from ceramic.

11. The electrosurgical instrument of claim 1, wherein a position of the channel forming a portion of the conduit of the aspiration system is maintained via an expanded material having been injected into a cavity between the channel and the shaft.

12. An electrosurgical instrument electrosurgical instrument for the treatment of tissue, comprising:
   a shaft;
   an electrode assembly, comprising:
      at least one active electrode;
      at least one return electrode separated from the active electrode via at least one insulator;
      the at least one insulator forming an internal aspiration collection chamber configured to received aspirated material from a surgical site and to pass the aspirated material on within the electrosurgical instrument;
      wherein the internal aspiration collection chamber is in fluid communication with at least one aspiration inlet; and an aspiration system for removing material from a surgical site, the aspiration system including at least one conduit formed by a channel extending through the shaft, the internal aspiration collection chamber and the at least one aspiration inlet;

wherein the at least one insulator includes a pocket into which a portion of a support arm of the active electrode extends, wherein a proximally facing surface of the active electrode contacts a distally facing surface of the at least one insulator and forces a proximally facing surface of the at least one insulator to contact a distally facing surface of the electrosurgical instrument, thereby securing the active electrode and the at least one insulator to the shaft of the electrosurgical instrument by enabling the support arm of the active electrode to secure the at least one insulator to the shaft of the electrosurgical instrument when the support arm of the active electrode is threaded onto the shaft of the electrosurgical instrument.

13. The electrosurgical instrument of claim 12, wherein the at least one insulator is coupled to a distal tip of the channel of the aspiration system and supports the at least one active electrode with a substantially planar outer surface that is nonorthogonal to a longitudinal axis of the channel of the aspiration system.

14. The electrosurgical instrument of claim 13, wherein the substantially planar outer surface of the at least one active electrode is positioned generally parallel to the longitudinal axis of the channel of the aspiration system.

15. The electrosurgical instrument of claim 12, wherein an outer surface of the active electrode is a sandblasted roughened surface.

16. An electrosurgical instrument for the treatment of tissue, comprising:
    a shaft;
    an electrode assembly, comprising:
        at least one active electrode;
        at least one return electrode separated from the active electrode via at least one insulator;
        the at least one insulator forming an internal aspiration collection chamber configured to received aspirated material from a surgical site and to pass the aspirated material on within the electrosurgical instrument;
        wherein the internal aspiration collection chamber is in fluid communication with at least one aspiration inlet;
    an aspiration system for removing material from a surgical site, the aspiration system including at least one conduit formed by a channel extending through the shaft, the internal aspiration collection chamber and the at least one aspiration inlet;
    wherein the at least one insulator is coupled to a distal tip of the channel of the aspiration system and supports the at least one active electrode with a substantially planar outer surface that is nonorthogonal to a longitudinal axis of the shaft of the electrosurgical instrument; and
    wherein the at least one active electrode includes a support arm extending from the substantially planar outer surface inwardly toward a longitudinal axis of the channel of the aspiration system whereby the support arm includes a threaded support orifice configured to be threadably attached to threads at a distal end of the channel of the aspiration system.

17. The electrosurgical instrument of claim 16, wherein the substantially planar outer surface of the at least one active electrode is positioned generally parallel to the longitudinal axis of the channel of the aspiration system, wherein the substantially outer surface of the at least one active electrode is separated from the shaft of the electrosurgical instrument by the at least one insulator, and wherein the threaded support orifice couples the internal aspiration collection chamber of the aspiration system to the at least one conduit of the aspiration system.

18. The electrosurgical instrument of claim 16, wherein the internal aspiration collection chamber is an elongated chamber defined at least in part by a distal, linear surface, a first proximal, linear surface and a second proximal, linear surface, wherein the distal, linear surface is aligned with the first and second proximal, linear surfaces and are each aligned with a longitudinal axis of the internal aspiration collection chamber, wherein the longitudinal axis of the internal aspiration collection chamber is positioned orthogonal to a longitudinal axis of the channel of the aspiration system, and wherein the internal aspiration collection chamber is formed from a first section and a second section, whereby the first section has a larger cross-sectional area than the second section and the first section is positioned closer to the at least one active electrode.

19. The electrosurgical instrument of claim 16, wherein the at least one insulator includes a pocket into which a portion of the support arm of the active electrode extends, wherein a proximally facing surface of the active electrode contacts a distally facing surface of the at least one insulator and forces a proximally facing surface of the at least one insulator to contact a distally facing surface of the electrosurgical instrument, thereby securing the active electrode and the at least one insulator to the shaft of the electrosurgical instrument by enabling the support arm of the active electrode to secure the at least one insulator to the shaft of the electrosurgical instrument when the support arm of the active electrode is threaded onto the shaft of the electrosurgical instrument.

20. The electrosurgical instrument of claim 16, wherein an outer surface of the active electrode is a sandblasted roughened surface, and wherein the at least one insulator is formed from ceramic.

* * * * *